(12) United States Patent  
Deshpande et al.

(10) Patent No.: US 7,652,147 B2
(45) Date of Patent: Jan. 26, 2010

(54) PROCESS FOR PREPARATION OF IRBESARTAN

(75) Inventors: Pandurang Balwant Deshpande, Vadodara (IN); Parven Kumar Luthra, Vadodara (IN); Dhiraj Mohansinh Rathod, Vadodara (IN); Hitesh Kantilal Patel, Vadodara (IN); Pinky Tarak Parikh, Vadodara (IN)

(73) Assignee: Alembic Limited, Vadodara, Gujarat (IN)

( * ) Notice: Subject to any disclaimer, the term of this patent is extended or adjusted under 35 U.S.C. 154(b) by 553 days.

(21) Appl. No.: 11/406,919

(22) Filed: Apr. 19, 2006

(65) Prior Publication Data

US 2007/0099973 A1 May 3, 2007

(30) Foreign Application Priority Data

Oct. 28, 2005  (IN) .................. 1360/MUM/2005

(51) Int. Cl.
*C07D 257/00* (2006.01)
*C07D 403/00* (2006.01)
(52) U.S. Cl. .................................. 548/250; 548/300.7
(58) Field of Classification Search ............. 548/250, 548/300.7
See application file for complete search history.

(56) References Cited

U.S. PATENT DOCUMENTS

| 5,270,317 | A |   | 12/1993 | Bernhart et al. |
| 5,352,788 | A |   | 10/1994 | Bernhart et al. |
| 5,559,233 | A | * | 9/1996 | Bernhart et al. ............. 544/321 |
| 2004/0192713 | A1 |   | 9/2004 | Nisnevich et al. |
| 2004/0242894 | A1 |   | 12/2004 | Dolitzky et al. |

FOREIGN PATENT DOCUMENTS

| CA | 2050769 | 3/1992 |
| WO | WO 91/14679 | 10/1991 |
| WO | WO 2005/113518 | 12/2005 |

OTHER PUBLICATIONS

Patani et al., Chem Rev, 1996, vol. 96 (8), especially p. 3148 and 3150.*

* cited by examiner

*Primary Examiner*—Golam M. M. Shameem
*Assistant Examiner*—Susannah Chung
(74) *Attorney, Agent, or Firm*—Volpe and Koenig, P.C.

(57) ABSTRACT

A process for the preparation of Irbesartan of formula (I)

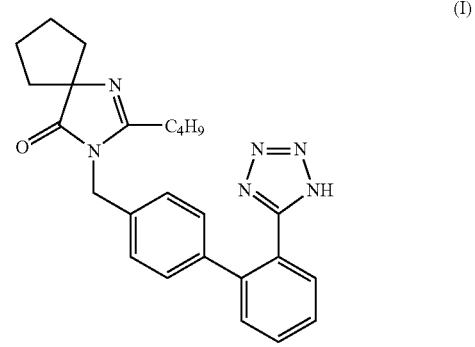

using the steps of:
(i) reacting 4' aminomethyl-2-cyano biphenyl of formula (VI) with 1-veleramido cyclopentane carboxylic acid of formula (V)

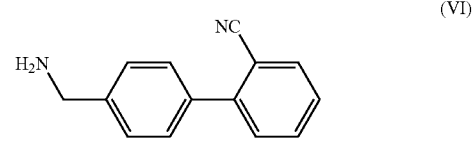

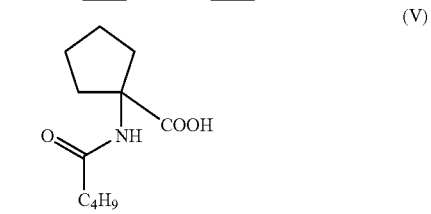

in an organic solvent and in the presence of an acid, without activating the —COOH group of compound of formula (V) to give 1-(2'cyanobiphenyl-4-yl-methylaminocarbonyl)-1-pentanoylamino cyclopentane of formula (VII).

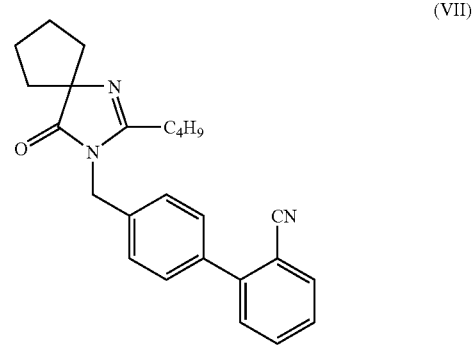

converting the compound of formula (VII) obtained in step (i) to Irbesartan of formula (I) by reacting the compound of the formula (VII) with tributyl tin azide in o-xylene to give Irbesartan of formula (I).

63 Claims, No Drawings

PROCESS FOR PREPARATION OF IRBESARTAN

FIELD OF THE INVENTION

The present invention relates to an improved process for preparing Irbesartan of formula (I).

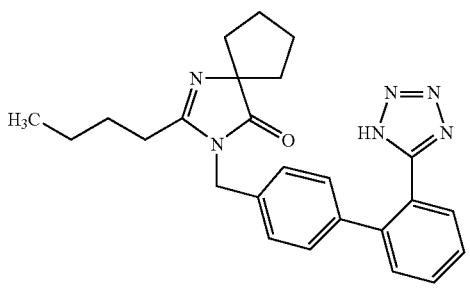

BACKGROUND OF THE INVENTION

The chemical name of Irbesartan is 2-Butyl-3-[[2'-(1H-tetrazol-5-yl)[1,1'-biphenyl]-4-yl]methyl]-1,3-diazaspiro[4,4]non-1-en-4-one and formula is $C_{25}H_{28}N_6O$ and molecular weight is 428.53. The current pharmaceutical product containing this drug is being sold by Sanofi Synthelabo using the tradename AVAPRO, in the form of tablets. Irbesartan is useful in the treatment of diabetic nefropathy, heart failure therapy and hypertension. Irbesartan is angiotension II type I ($AII_1$)-receptor antagonist. Angiotension II is the principal pressor agent of the rennin-angiotension system and also stimulates aldosterone synthesis and secretion by adrenal cortex, cardiac contraction, renal resorption of sodium, activity of the sympathetic nervous system and smooth muscle cell growth. Irbesartan blocks the vasoconstrictor and aldosterone-secreting effects of angiotension II by selectively binding to the $AT_1$ angiotension II receptor.

U.S. Pat. Nos. 5,270,317 and 5,559,233 describes a process for the preparation of N-substituted heterocyclic derivatives which involves reacting a heterocyclic compound of the formula

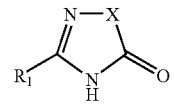

with a (biphenyl-4-yl)methyl derivative of the formula

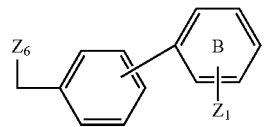

wherein $R_1$, $R_2$, $R_3$, $R_4$, $R_5$, and t, z and Hal have the meanings given in said U.S. Pat. No. 5,270,317, in the presence of an inert solvent such as DMF, DMSO or THF, with a basic reagent, for example KOH, a metal alcoholate, a metal hydride, calcium carbonate or triethylamine. The products of the reaction were purified by chromatography.

U.S. Pat. Nos. 5,352,788, and 5,559,233, and WO 91/14679 also describe identical alkylation of the nitrogen atom of the heterocyclic compound with the halo-biphenyl compound using the same inert solvent and the same basic reagents.

Also Canadian Patent No. 2050769 describes the alkylation of the nitrogen atom of the heterocycle of the formula

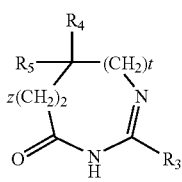

with a compound of the formula

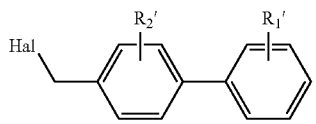

wherein X, $R_1$, $Z_1$ and $Z_6$ have the meanings given therein, in the presence of N,N-dimethylformamide and a basic reagent, such as alkali metal hydrides for example sodium or potassium hydride.

All of the above identified patents describe alkylation in solvents, such as N,N-dimethylformamide or DMSO, etc. in the presence of a basic reagent, for example, a metal hydride or a metal alcoholate etc. The strong bases, such as metal hydride or a metal alcoholate require anhydrous reaction conditions. Since N,N-dimethylformamide is used as a solvent, its removal requires high temperature concentration by distillation, which can result in degradation of the final product. The product intermediate is also purified by chromatography which is commercially not feasible and cumbersome on large scale.

Another process given in Canadian Patent No. 2050769 provides synthetic scheme as herein given below.
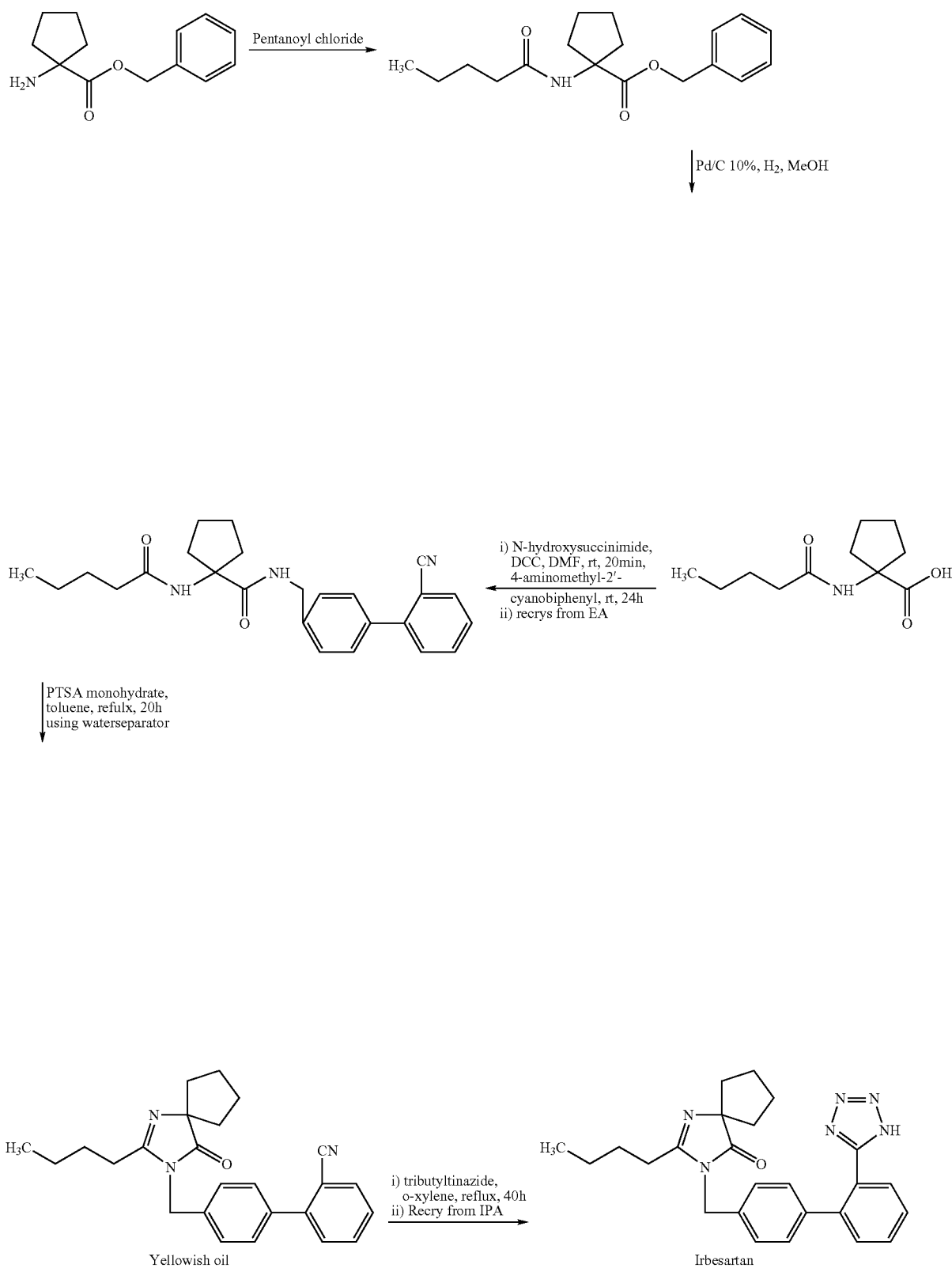

This process comprises the steps of protecting carboxylic group present on cyclopentane ring which is deprotected in consecutive step by vigourous hydrogenation condition in autoclave which is operationally difficult at a large scale.

US Patent No. 2004242894 also discloses the process of preparation of Irbesartan from 4-bromomethyl biphenyl 2'-(1H-tetrazol (2-triphenylmethyl) 5-yl) and Ethyl ester of 1-Valeramido cyclopentanecarboxylic acid in toluene in presence of base and PTC, and then hydrolyzing the protecting group. However this requires chromatographic purification.

This patent also discloses the process of preparation of tetrazolyl protected Irbesartan using 2,6 lutidine and oxalylchloride in toluene. However in this process the yield is as low as 30%.

US Patent No. 2004192713 discloses the process of preparation of Irbesartan by condensing the two intermediates via Suzuki coupling reaction. The reaction scheme is as given herein below.

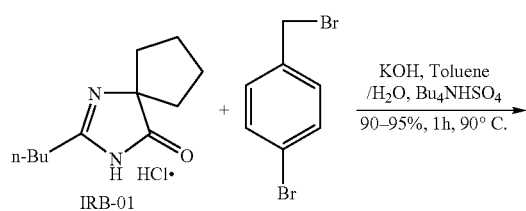

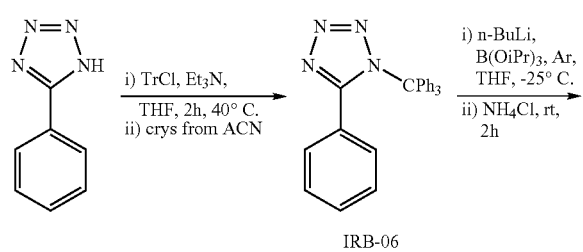

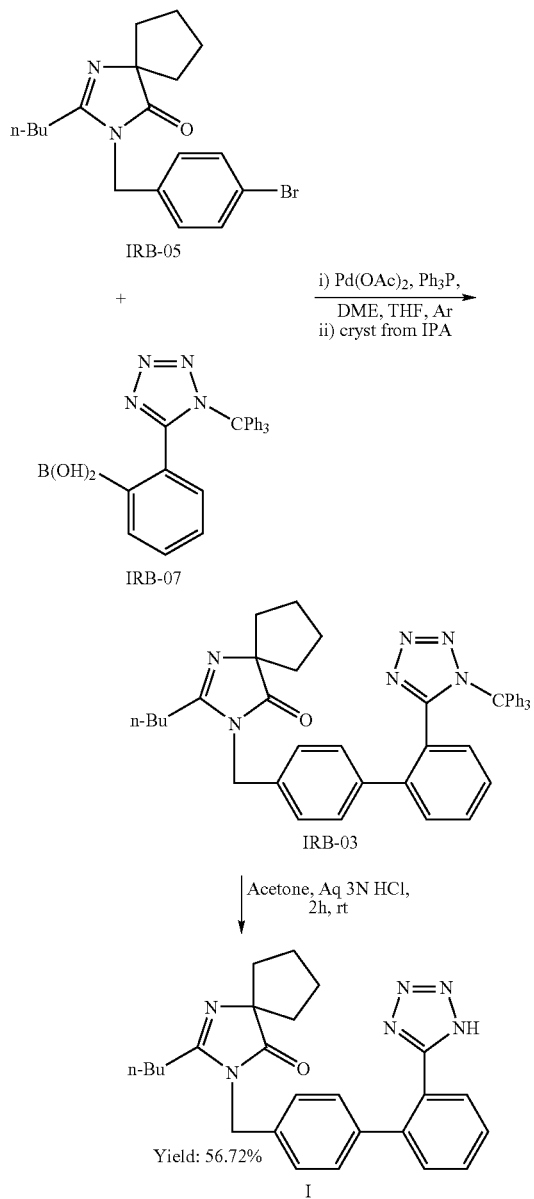

However, this process has several disadvantages such as use of the reagents like butyl lithium and triisobutyl borate at low temp such as −20 to −30° C. under Argon atmosphere condition which is difficult to maintain at commercial scale.

WO2005113518 discloses the process of preparation of Irbesartan by condensing n-pentanoyl cycloleucine (V) with 2-(4-aminomethyl phenyl) benzonitrile (VI) using dicyclocarbodiimide (DCC) and 1-hydroxy benzotriazole as catalyst to give an open chain intermediate of formula (VIII) which is then cyclized in the presence of an acid, preferably trifluoro acetic acid to give cyano derivative of formula (VII) and which in turn is converted to Irbesartan by treating it with tributyl tin chloride and sodium azide.

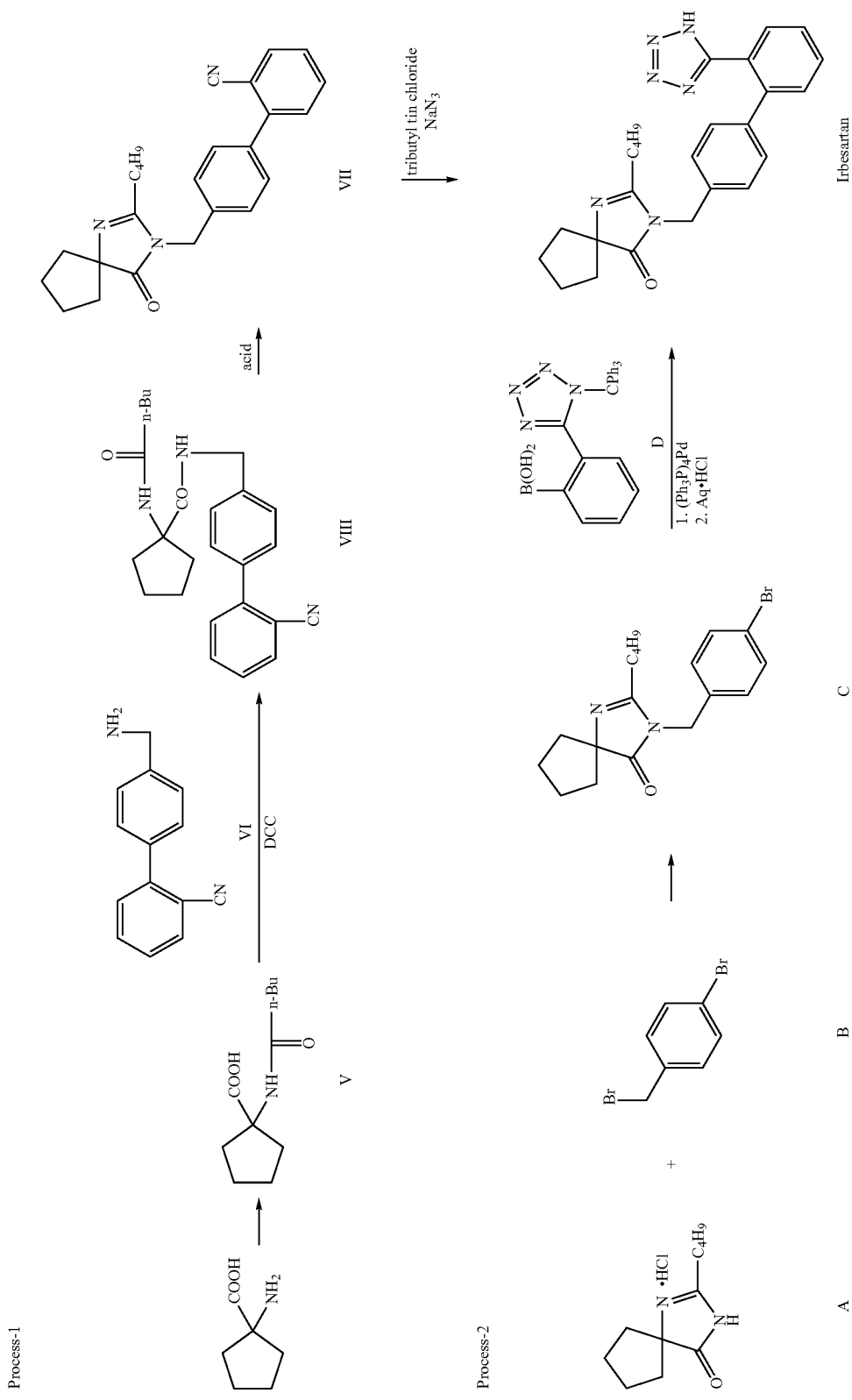

In this application further describes another process comprising the steps of reacting 2-butyl-1,3-diazaspiro[4,4]non-1-en-4-one monohydrochloride (A) with 4-bromobenzyl bromide (B) in presence of base and solvent to give 3-[4-bromobenzyl]-2-butyl-1,3-diazaspiro[4,4]non-1-en-4-one (C) which is condensed with 2-[2'-(triphenylmethyl-2'H-tetrazol-5'-yl)phenyl boronic acid in the presence of tetrakis triphenyl phosphine palladium and base to give Irbesartan (I).

However these processes suffer with several disadvantages such as it uses trifluoroacetic acid for the cyclization step which is highly corrosive material. The process requires an additional step of activation by DCC. This step not only increases number of steps but also create problem in handling DCC at an industrial scale as it is highly prone to hazard which makes the process least preferred on a large scale production of Irbesartan. Further it uses phenyl boronic acid derivative and triphenyl phosphine complex which are harmful for the skin and eye tissue and also harmful for respiratory system. Tetrakis triphenyl phosphine palladium is also a costly material which increases overall cost for the production of Irbesartan. Moreover the yield is as low as 22%.

All the above patents/applications are incorporated herein as reference.

In summary, prior art relating to the process for the preparation of Irbesartan suffers with several drawbacks such as i) It requires chromatographic purification of intermediates at various stages.
ii) It requires specific autoclave conditions for a deprotection of protecting group.
iii) It requires maintaining low temperature conditions such as −30° C. and requires special handling care and air and moisture tight condition with the reagents such as butyl lithium and triisobutyl borate.
iv) It uses hazardous and highly corrosive reagents.
v) It suffers low yield problem.
vi) All the process is having more number of reaction steps.

It is therefore, a need to develop a process which not only overcomes the disadvantages of the prior art but also economical, operationally simple and industrially applicable. Present inventors have directed their research work towards developing a process for the preparation of Irbesartan which is devoid of the above disadvantages.

OBJECTS OF THE INVENTION

It is therefore an object of the present invention is to provide an improved process for the preparation of Irbesartan.

Another object of the present invention is to provide an improved process for the preparation of intermediate 1-valeramido cyclopentanecarboxylic acid which is used in the process of preparation of Irbesartan.

Another object of the present invention is to provide a process which is simple and easy to handle at an industrial scale.

A further object of the present invention is to provide a process which eliminates the use of chromatographic purification at intermediate stages and provides such kind of purification which is feasible at commercial scale.

Yet another object of the present invention is to provide a process which involves less number of steps to produce Irbesartan (I).

Yet another object of the present invention is to provide a process for the preparation of Irbasartan comprising step of reacting 4' aminomethyl-2-cyano biphenyl of formula (VI) with 1-veleramido cyclopentane carboxylic acid (V) in an organic solvent and in the presence of acid.

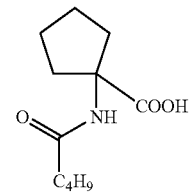

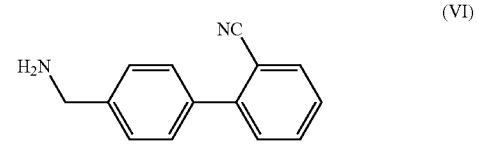

Yet another object of the present invention is to provide a process for the preparation of Irbesartan without activation the —COOH group of compound of formula (V).

Yet another object of the present invention is to provide a process for the preparation of Irbesartan which does not involve isolation step of open chain compound of formula VIII and also without activating —COOH group of compound of formula (V).

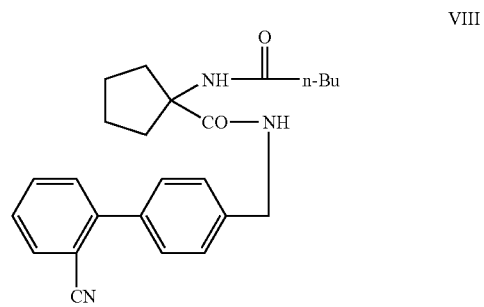

SUMMARY OF THE INVENTION

Accordingly, present invention provides an improved process of preparation of Irbesartan comprising steps of:

(i) reacting 4' aminomethyl-2-cyano biphenyl of formula (VI) with 1-veleramido cyclopentane carboxylic acid (V) in an organic solvent and in the presence of acid to obtain the compound of the formula (VII).

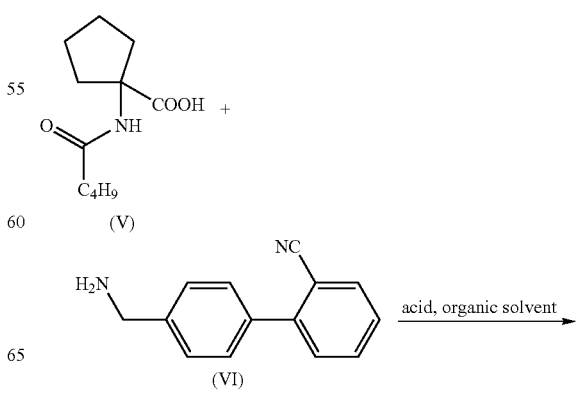

-continued

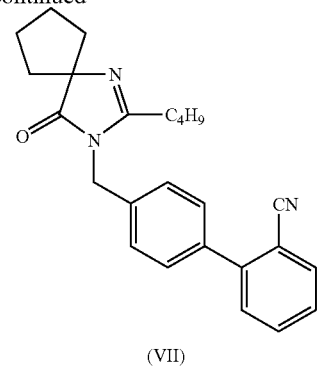

(VII)

(ii) reacting the compound of the formula (VII) with tributyl tin azide in an organic solvent at elevated temperature to provide Irbesartan of formula (I).

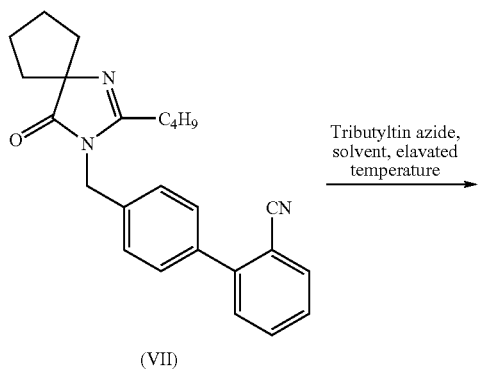

(VII)

Tributyltin azide, solvent, elavated temperature →

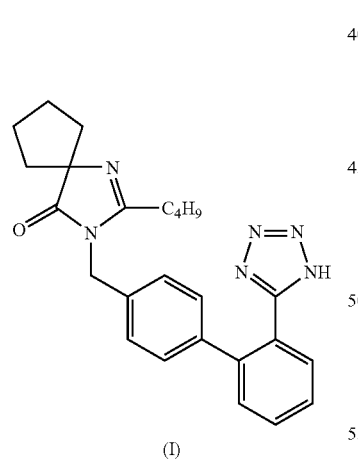

(I)

DETAILED DESCRIPTION OF THE INVENTION

The present invention provides an improved process of preparation of Irbesartan comprising steps of:

(i) reacting 4' aminomethyl-2-cyano biphenyl of formula (VI) with 1-veleramido cyclopentane carboxylic acid (V) in an organic solvent and in the presence of acid to obtain the compound of the formula (VII).

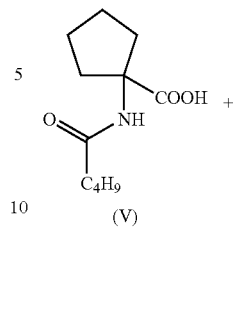

(V)

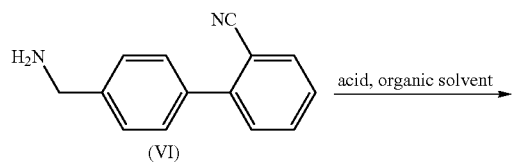

(VI)

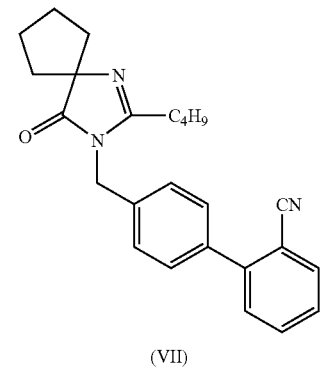

(VII)

(ii) reacting the compound of the formula (VII) with tributyl tin azide in an organic solvent at elevated temperature to provide Irbesartan of formula (I).

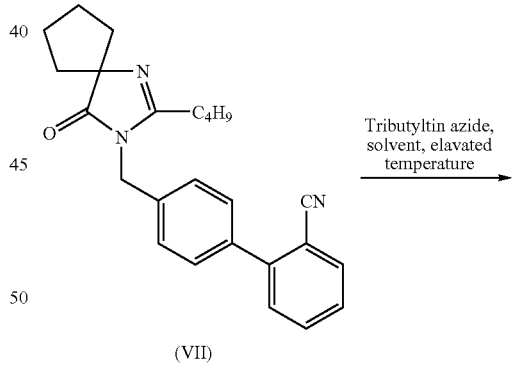

(VII)

Tributyltin azide, solvent, elavated temperature →

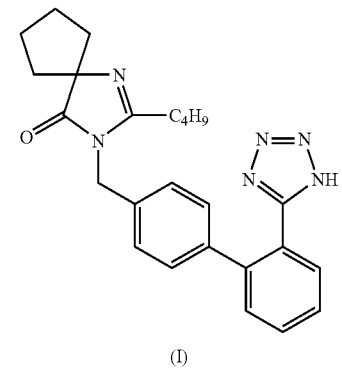

(I)

The reaction in step (i) is carried out at a temperature equal to the boiling point of the solution. In general it is in the range of from about 100° C. to about 150° C. The water which is liberated during the course of the reaction is removed from the reaction mixture by methods such as azeotropic distillation or using an apparatus such as dean stark or by any conventional methods known in the art.

The solvent mentioned hereinabove is such that it should be capable of removing the water azeotropically.

The example of "organic solvent" as mentioned hereinabove includes but not limited to $C_{1-8}$ hydrocarbons such as toluene, xylene and the like or the mixture thereof.

The example of the "acid" as mentioned hereinabove includes but not limited to methane sulfonic acid, p-toluene sulfonic acid, sulfuric acid and the like or the mixture thereof.

After the completion of reaction the solvent is removed from the reaction mass by distillation either under vacuum or atmospheric pressure. The residue is dissolved in solvent such as Ethyl acetate, dichloromethane, chloroform and the like which is then washed with base solution. Base is selected from the group comprising NaOH, KOH, LiOH, NaHCO$_3$, KHCO$_3$, Na$_2$CO$_3$, K$_2$CO$_3$ and the like or mixture thereof. Organic phase is separated and distilled out completely under vacuum. The residue is leached with non-polar solvent which includes but not limited to Methyl t-butyl ether, diisopropyl ether, diethylether, cyclohexane and the like or mixture thereof. The product is isolated by filtration or decandation or centrifugal methods.

The solid is dried under vacuum at 50-60° C. to give compound of formula (VII).

The conversion of cyano group to tetrazolyl group of Irbesartan is done as per the methods known in the art.

In the reaction in step (ii), compound (VII) obtained in step (i) is reacted with tributyl tin azide in organic solvent such as o-xylene at reflux temperature for 80 hours to give the crude Irbesartan.

The mass is treated with 1N NaOH. The phases were separated and aq. phase is washed with o-xylene and isopropyl ether. Aqueous phase is treated with charcoal, filtered through hyflobed and then treated with 3N HCl. The product title compound is filtered, washed with water and dried under vacuum at 60° C. The product is crystallized from 95% ethanol to give Irbesartan of formula (I).

Starting material 1-veleramidocyclopentane carboxylic acid of formula (V) is prepared by reacting Aminocyclopentane carboxylic acid hydrochloride salt of formula (IV) with valeroyl chloride in the presence of pyridine.

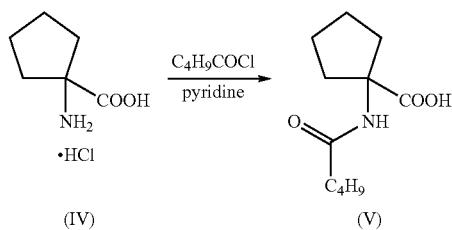

In another embodiment of the present invention, the starting material 1-veleramido cyclopentane carboxylic acid of formula (V) is prepared by an improved process which comprises reacting Aminocyclopentane carboxylic acid hydrochloride salt of formula (IV)

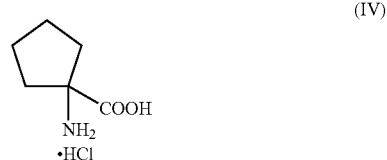

with valeroyl chloride in the presence of a base and a phase transfer catalyst (PTC) in a suitable solvent to give 1-veleramido cyclopentane carboxylic acid of formula (V).

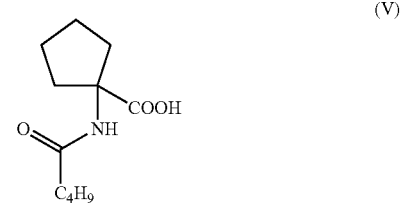

The example of the PTC as mentioned hereinabove includes but not limited to quarternery ammonium compound, phosphonium compound and cyclic polyethers such as tetrabutyl ammonium bromide (TBAB), tetrabutyl ammonium hydrogensulfate, benzalkonium chloride, cetyl trimethyl ammonium chloride, and the like or the mixture thereof.

The suitable solvent as mentioned hereinabove is selected from the group of non polar water immisible solvent.

The example of the non polar water immisible solvent mentioned hereinabove includes but not limited to toluene, xylene, benzene, dichloromethane, cyclohexane, hexane, heptane and the like or the mixture thereof.

The example of the base as mentioned hereinabove is selected from the group comprising alkali metal hydroxide, alkaline earth metal carbonate or bicarbonate such as NaOH or KOH, LiOH, Na$_2$CO$_3$, K$_2$CO$_3$, KHCO$_3$, NaHCO$_3$, CaCO$_3$ and the like or mixture thereof.

In another embodiment, the process of preparation of Irbesartan comprises the steps of:
(i) reacting Cyclopentanone of formula (II) with sodium cyanide in the presence of ammonium chloride and aqueous ammonia in methanol to give the 1-Aminocyclopentane carbonitrile of formula (III).

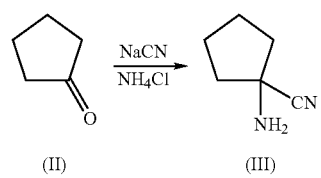

(ii) reacting 1-Aminocyclopentane carbonitrile of formula (III) obtained in above step (i) with aqueous HCl to give 1-Amino cyclopentane carboxylic acid as hydrochloride salt of formula (IV)

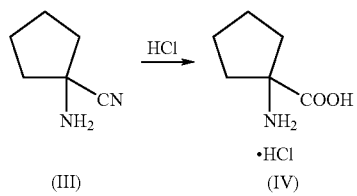

(iii) reacting Aminocyclopentane carboxylic acid hydrochloride salt of formula (IV) obtained in above step (ii) with valeroyl chloride in the presence of base and phase transfer catalyst in a suitable solvent and water to give 1-veleramido cyclopentane carboxylic acid of formula (V);

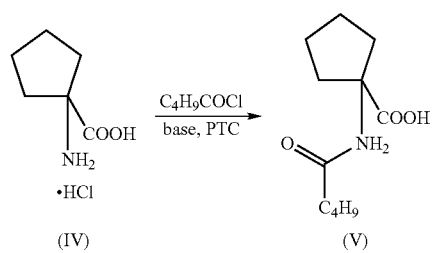

wherein the said PTC is tetrabutyl ammonium bromide, the said solvent is toluene and the said base is NaOH.

(iv) reacting 1-veleramidocyclopentanecarboxylic acid compound of formula (V) obtained in above step (iii) with 4' aminomethyl-2-cyano biphenyl of formula (VI) in a solvent such as toluene and in the presence of methane sulfonic acid to give compound of formula (VII).

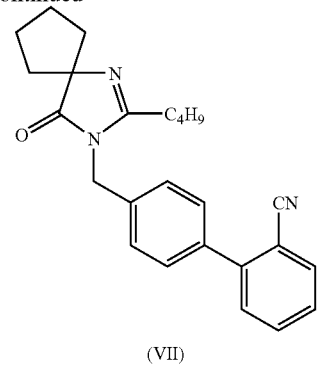

(v) reacting 2-(n-Butyl)-3-(2'-cyanobiphenyl-4-ylmethyl)-4-oxo-1,3 diazaspiro[4.4]non-1-ene-4-one of formula (VII) obtained in above step (iv) with tributyl tin azide in o-xylene to give the title compound Irbesartan of formula (I).

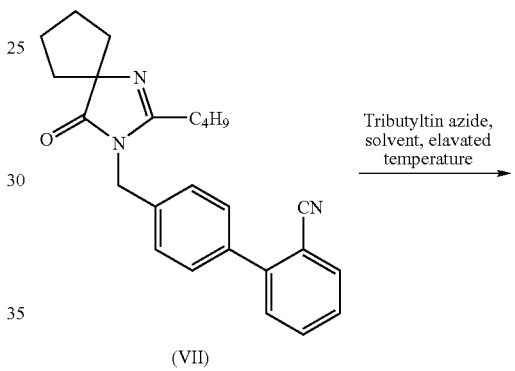

In another embodiment of the present invention, an improved process for the preparation of Irbesartan comprises steps of:

(i) reacting biphenyl derivative of formula (VIa) with 1-veleramido cyclopentane carboxylic acid (V) in an organic solvent and in the presence of an acid to obtain the compound of the formula (VIIa).

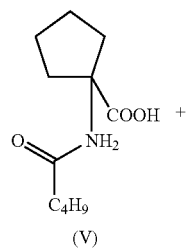

(V)

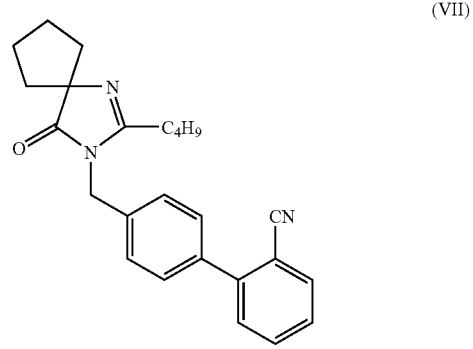

(VIa)

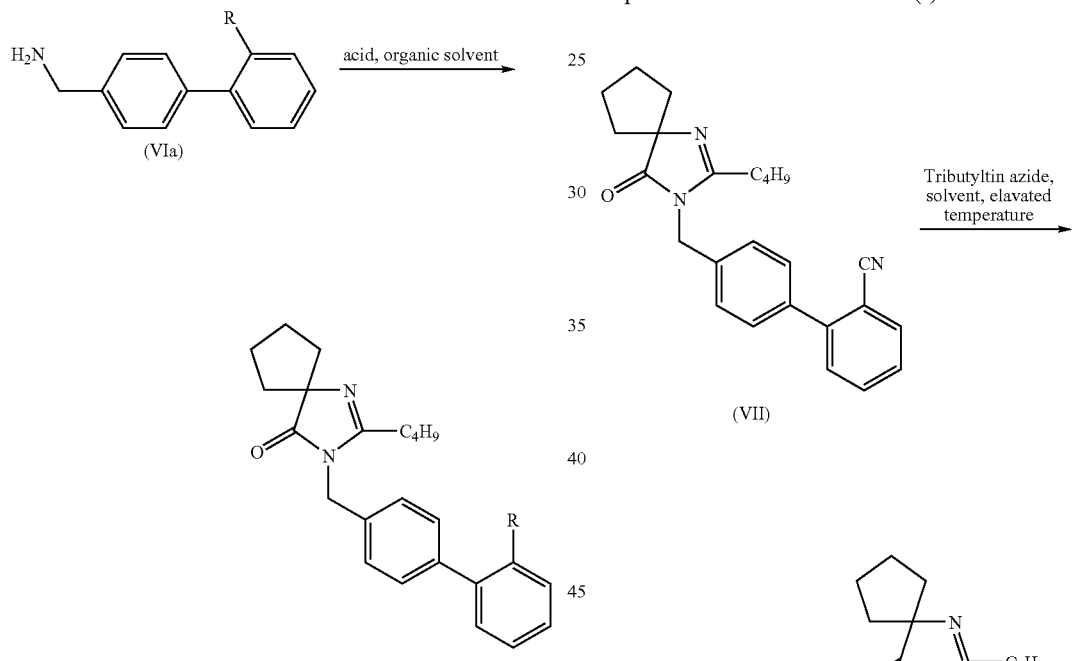

(VIIIa)

wherein R represents the group selected from —CONH₂ or compound of formula

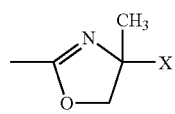

where X is H or $C_{1-4}$ alkyl; preferably methyl;

or any other such group which can be converted to cyano group, wherein the said "acid" and "organic solvent" is selected from the group as defined earlier.

(ii) converting the compound of formula (VIIa) to compound of formula (VII).

(VII)

(iii) reacting the compound of the formula (VII) with tributyl tin azide in an organic solvent at elevated temperature to provide Irbesartan of formula (I).

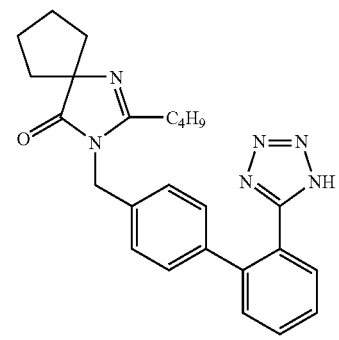

(I)

The conversion of compound of formula (VIIa) to compound of formula (VII) is performed by conventional methods known in the art.

When R represents —CONH₂, the conversion of compound of formula (VIIa) to compound of formula (VII) is carried out in the presence of thionyl chloride.

When R represents compound of formula

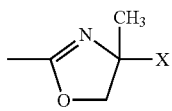

wherein X has the same meaning given above; the conversion of compound of formula (VIIa) to compound of formula (VII) is carried out in polar solvent and in the presence of phosphorous oxychloride.

In another embodiment of the present invention, it provides an improved process for the preparation of Irbesartan comprises steps of:
(i) reacting biphenyl derivative of formula (VIb) with 1-veleramido cyclopentane carboxylic acid (V) in an organic solvent and in the presence of an acid to obtain the compound of the formula (VIIb).

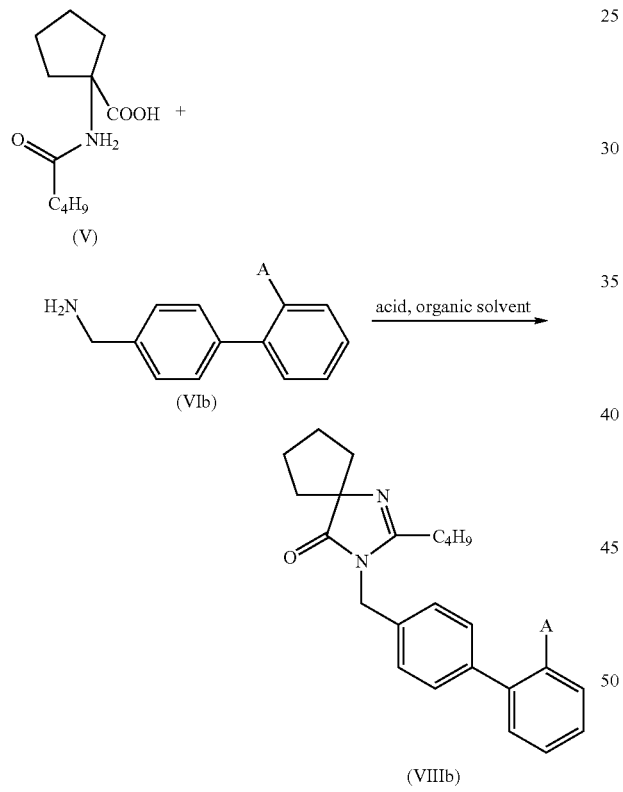

wherein A represents protected tetrazolyl group.

Suitable protecting groups of protected 1H-tetrazol-5-yl are the protecting groups customarily used in tetrazole chemistry, especially triphenylmethyl, unsubstituted or substituted, for example nitro-substituted, benzyl, such as 4-nitrobenzyl, lower alkoxymethyl, such as methoxymethyl or ethoxymethyl, lower alkylthiomethyl, such as methylthiomethyl, and 2-cyanoethyl, also lower alkoxy-lower alkoxymethyl, such as 2-methoxyethoxymethyl, benzyloxymethyl and phenacyl.

wherein the said "acid" and "organic solvent" is selected from the group as defined earlier.
(ii) deprotecting the protected tetrazolyl group present in the compound of formula (VIIb) by known methods to get Irbesartan of formula (I)

For example triphenylmethyl is customarily removed by means of hydrolysis especially in the presence of an acid, for example in the presence of hydrogen halide, advantageously in an inert solvent, such as haloalkane or an ether, for example in dichloromethane or dioxane, and with heating; or by hydrogenolysis in the presence of hydrogenation catalyst, 4-nitrobenzyl is removed, for example by hydrogenolysis in the presence of hydrogenation catalyst; methoxymethyl or ethoxymethyl is removed, for example by treatment with a lower alkyl tin bromide such as triethyl- or tributyl-tin bromide; methylthiomethyl is removed for example by treatment with trifluoroacetic acid; 2-cyanoethyl is removed, for example, by hydrolysis, for example with hydrochloric acid; and benzyloxymethyl and phenacyl are removed, for example by hydrogenolysis in the presence of a hydrogenation catalyst.

In another embodiment of the present invention, an improved process for the preparation of Irbesartan comprises steps of:
(i) reacting 4' aminomethyl-2-cyano biphenyl of formula (VI) with 1-veleramido cyclopentane carboxylic acid of formula (V)

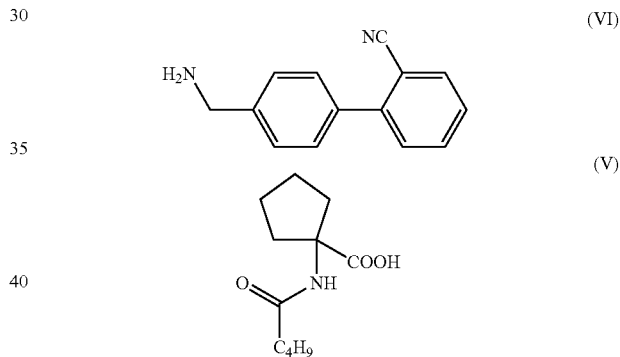

in toluene and in the presence of methane sulfonic acid, without activating the —COOH group of compound of formula (V) and without isolating open chain compound of formula (VIII) to give 1-(2'cyanobiphenyl-4-yl-methylaminocarbonyl)-1-pentanoylamino cyclopentane of formula (VII).

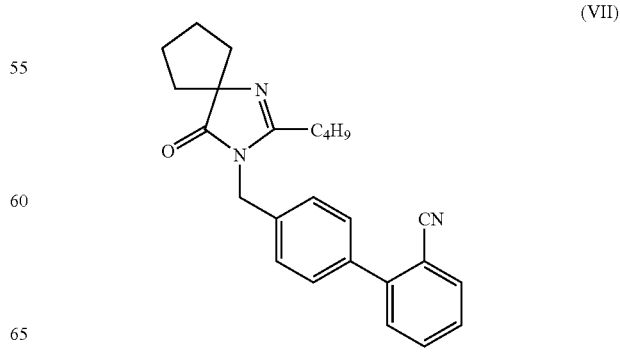

(ii) converting the compound of formula (VII) obtained in step (i) to Irbesartan of formula (I) by reacting the compound of the formula (VII) with tributyl tin azide in o-xylene to give Irbesartan of formula (I).

The process of the present invention has following advantages:
  (i) It eliminates the requirement of chromatographic purification of intermediates at various stages and provides a process which is economical, operationally simple and industrially applicable.
  (ii) The process provides less number of steps as it eliminates the steps of protection and deprotection.
  (iii) The process is simple and easy to handle and does not require special handling care or critical temperature conditions.
  (iv) It eliminates the use of reagents which is greatly air and moisture sensitive.
  (v) It does not require tedious step of activation of carboxylic group of compound of formula (V) using dicyclocarbodiimide (DCC) which is not only difficult in handling but highly prone to hazard.

The following examples illustrate the invention further and do not limit the scope of the invention in any manner.

Example 1

Preparation of 2-(n-Butyl)-3-(2'-cyanobiphenyl-4-ylmethyl)-4-oxo-1,3 diazaspiro[4.4]non-1-ene-4-one 4'aminomethyl-2-cyano biphenyl (50 g) (VI) is added to toluene (2 Liter) and methane sulfonic acid (19 ml) and stirred at ambient temperature.
1-Valeramidocyclopentanecarboxylic acid (56.3 g) (V) is added to the above solution and the mass is refluxed under stirring for 24 hours and water is separated by dean stark apparatus. Methane sulphonic acid (4 ml) is added to the reaction mixture and refluxed under stirring for 24 hours and water is separated by dean stark apparatus. The reaction mixture is cooled to ambient temperature and toluene is distilled under vacuum completely. Ethyl acetate (2 Liter) and 2N sodium hydroxide solution (320 ml) is added to the residue and stirred for 30 minutes. Two phases are separated and the organic phase is washed with brine (400 ml). The organic phase is treated with activated charcoal, filtered through hyflobed and filtrate is distilled out under vacuum completely. Methyl t-butyl ether (123 ml) is added to the residue and stirred for 2 hours at ambient temperature. The product is filtered and washed with methyl t-butyl ether (90 ml) and suck dried. The product is dried under vacuum at 50° C. till constant weight. (Yield: 88%)
$^1$H-NMR (CDCl$_3$): δppm 0.83 (t, 3H); 1.24-136 (sex, 2H); 1.51-1.61 (quent, 2H); 1.78-1.98 (m, 10H); 2.32 (t, 2H); 4.71 (s, 2H); 7.24-7.73 (m, 8H)

Example 2

Preparation of 2-(n-Butyl)-3-(2'-cyanobiphenyl-4-ylmethyl)-4-oxo-1,3 diazaspiro[4.4]non-1-ene-4-one 4'aminomethyl-2-cyano biphenyl (50 g) (VI) is added to toluene (2 Liter) and methane sulfonic acid (19 ml) and stirred it at ambient temperature.
1-Valeramidocyclopentanecarboxylic acid (56.3 g) (V) is added to the above solution and the mass is refluxed under stirring for 24 hours and water is separated by dean stark apparatus. Methane sulphonic acid (4 ml) is added to the reaction mixture and refluxed under stirring for 24 hours and water is separated by dean stark apparatus. The reaction mixture is cooled to ambient temperature and 2N sodium hydroxide solution (320 ml) is added to the residue and stirred for 30 minutes. Two phases are separated and the organic phase is washed with brine (400 ml). The organic phase is treated with activated charcoal, filtered through hyflobed and filtrate is distilled out under vacuum completely. Methyl t-butyl ether (123 ml) is added to the residue and stirred for 2 hours at ambient temperature. The product is filtered and washed with methyl t-butyl ether (90 ml) and suck dried. The product is dried under vacuum at 50° C. till constant weight. (Yield: 90%)
$^1$H-NMR (CDCl$_3$): δppm 0.83 (t, 3H); 1.24-136 (sex, 2H); 1.51-1.61 (quent, 2H); 1.78-1.98 (m, 10H); 2.32 (t, 2H); 4.71 (s, 2H); 7.24-7.73 (m, 8H)

Example 3

Preparation of 2-(n-Butyl)-3-(2'-cyanobiphenyl-4-ylmethyl)-4-oxo-1,3 diazaspiro[4.4]non-1-ene-4-one 4'aminomethyl-2-cyano biphenyl (50 g) (VI) is added to xylene (2 Liter) and methane sulfonic acid (19 ml) and stirred it at ambient temperature.
1-Valeramidocyclopentanecarboxylic acid (56.3 g) (V) is added to the above solution and the mass is refluxed under stirring for 24 hours and water is separated by dean stark apparatus. Methane sulphonic acid (4 ml) is added to the reaction mixture and refluxed under stirring for 24 hours and water is separated by dean stark apparatus. The reaction mixture is cooled to ambient temperature and 2N sodium hydroxide solution (320 ml) is added to the residue and stirred for 30 minutes. Two phases are separated and the organic phase is washed with brine (400 ml). The organic phase is treated with activated charcoal, filtered through hyflobed and filtrate is distilled out under vacuum completely. Diisopropyl ether (123 ml) is added to the residue and stirred for 2 hours at ambient temperature. The product is filtered and washed with diisopropyl ether (90 ml) and suck dried. The product is dried under vacuum at 50° C. till constant weight. (Yield: 88%)
$^1$H-NMR (CDCl$_3$): δppm 0.83 (t, 3H); 1.24-136 (sex, 2H); 1.51-1.61 (quent, 2H); 1.78-1.98 (m, 10H); 2.32 (t, 2H); 4.71 (s, 2H); 7.24-7.73 (m, 8H)

Example 4

Preparation of 2-(n-Butyl)-3-(2'-cyanobiphenyl-4-ylmethyl)-4-oxo-1,3 diazaspiro[4.4]non-1-ene-4-one 4'aminomethyl-2-cyano biphenyl (50 g) (VI) is added to xylene (2 Liter) and p-toluene sulfonic acid (54.8 g) and stirred it at ambient temperature.
1-Valeramidocyclopentanecarboxylic acid (56.3 g) (V) is added to the above solution and the mass is refluxed under stirring for 24 hours and water is separated by dean stark apparatus. P-toluene sulfonic acid (13.7 g) is added to the reaction mixture and refluxed under stirring for 24 hours and water is separated by dean stark apparatus. The reaction mixture is cooled to ambient temperature and 2N potassium hydroxide solution (320 ml) is added to the residue and stirred for 30 minutes. Two phases are separated and the organic phase is washed with brine (400 ml). The organic phase is treated with activated charcoal, filtered through hyflobed and filtrate is distilled out under vacuum completely. Diisopropyl ether (123 ml) is added to the residue and stirred for 2 hours at ambient temperature. The product is filtered and washed with diisopropyl ether (90 ml) and suck dried. The product is dried under vacuum at 50° C. till constant weight. (Yield: 84%)

¹H-NMR (CDCl₃): δppm 0.83 (t, 3H); 1.24-136 (sex, 2H); 1.51-1.61 (quent, 2H); 1.78-1.98 (m, 10H); 2.32 (t, 2H); 4.71 (s, 2H); 7.24-7.73 (m, 8H)

Example 5

Preparation of Irbesartan

Cyclopentanone of formula (II) is reacted with sodium cyanide in the presence of ammonium chloride and aqueous ammonia in methanol and water at 60° C. for 1-1.5 hours. The mass is extracted with dichloromethane whereupon the removal of the solvent provides 1-Aminocyclopentane carbonitrile.

1-Aminocyclopentane carbonitrile of formula (III) obtained in above step is treated with aq. HCl at 100° C. for 24 hours. The mass is cooled to 0° C. and filtered the solid. The solid is dissolved in water at 90-95° C. Activated charcoal is added and stirred. The solution is filtered through hyflow bed. The pH of the solution is adjusted 5 with TEA. The mass is cooled to 0-5° C. and stirred for 2 hours whereupon the product is precipitate out which is filtered to give 1-Amino cyclopentane carboxylic acid as hydrochloride salt.

1-Aminocyclopentane carboxylic acid hydrochloride of formula (IV) obtained in above step is treated with valeroyl chloride in the presence of tetrabutyl ammonium bromide and aqueous sodium hydroxide solution at 0-5° C. for 1 hours. The reaction mix was diluted with water and toluene and separated the two phases. The aqueous phase was washed with toluene, chilled and then acidified to give precipitate. The solid was filtrated and washed with water to give 1-veleramido cyclopentane carboxylic acid.

4'aminomethyl-2-cyano biphenyl (50 g) (VI) is added to toluene (2 Liter) and p-toluene sulfonic acid (54.8 g) and stirred it at ambient temperature.

1-Valeramidocyclopentanecarboxylic acid (56.3 g) (V) obtained in above step is added to the above solution and the mass is refluxed under stirring for 24 hours and water is separated by dean stark apparatus. P-toluene sulfonic acid (13.7 g) is added to the reaction mixture and refluxed under stirring for 24 hours and water is separated by dean stark apparatus. The reaction mixture is cooled to ambient temperature and 2N sodium hydroxide solution (320 ml) is added to the residue and stirred for 30 minutes. Two phases are separated and the organic phase is washed with brine (400 ml). The organic phase is treated with activated charcoal, filtered through hyflobed and filtrate is distilled out under vacuum completely. Methyl t-butyl ether (123 ml) is added to the residue and stirred for 2 hours at ambient temperature. The product is filtered and washed with methyl t-butyl ether (90 ml) and suck dried. The product is dried under vacuum at 50° C. till constant weight. (Yield: 88%)

2-(n-Butyl)-3-(2'-cyanobiphenyl-4-ylmethyl)-4-oxo-1,3 diazaspiro[4.4]non-1-ene-4-one of formula (VII) obtained in above step is reacted with tributyl tin azide in o-xylene at reflux temperature for 80 hours to give crude Irbesartan. The mass is treated with 1N NaOH. The phases were separated and aq. phase is washed with o-xylene and isopropyl ether. Aq phase is treated with charcoal, filtered through hyflobed and then treated with 3N HCl. The product title compound is filtered, washed with water and dried under vacuum at 60° C. The product is crystallized from 95% ethanol to give Irbesartan. (Yield: 86%).

¹H-NMR (DMSO d6): δppm 0.78 (t, 3H); 1.17-1.30 (sex, 2H); 1.40-1.50 (quent, 2H); 1.64-1.66 (m, 2H); 1.80-1.82 (m, 6H); 2.22-2.29 (t, 2H); 4.67 (s, 2H); 7.07 (s, 4H); 7.50-7.68 (m, 4H)

M⁺: 429.6

Example 6

Preparation of Irbesartan

4'aminomethyl-2-(1,3-oxazolin-4,4-dimethyl)-1,1' biphenyl (67.2 g) (VIa, where R is 1,3-oxazolin-4,4-dimethyl-2-yl) is added to toluene (2 Liter) and methane sulfonic acid (19 ml) and stir it at ambient temperature.

1-Valeramidocyclopentanecarboxylic acid (56.3 g) (V) is added to the above solution and the mass is refluxed under stirring for 24 hours and water is separated by dean stark apparatus. Methane sulphonic acid (4 ml) is added to the reaction mixture and refluxed under stirring for 24 hours and water is separated by dean stark apparatus. The reaction mixture is cooled to ambient temperature and toluene is distilled under vacuum completely. Ethyl acetate (2 Liter) and saturated sodium bicarbonate solution (320 ml) is added to the residue and stirred for 30 minutes. Two phases are separated and the organic phase is washed with brine (400 ml). The organic phase is treated with activated charcoal, filtered through hyflobed and filtrate is distilled out under vacuum completely. Methyl t-butyl ether (123 ml) is added to the residue and stirred for 2 hours at ambient temperature. The product is filtered and washed with methyl t-butyl ether (90 ml) and suck dried. The product is dried under vacuum at 50° C. till constant weight. (Yield: 80%) to give 2-(n-Butyl)-3-[2' (1,3-oxazolin-4,4-dimethyl)-biphenyl-4-ylmethyl]-4-oxo-1,3 diazaspiro[4.4]non-1-ene-4-one.

2-(n-Butyl)-3-[2'(1,3-oxazolin-4,4-dimethyl)-biphenyl-4-ylmethyl]-4-oxo-1,3 diazaspiro[4.4]non-1-ene-4-one of formula (VIIa, where R is 1,3-oxazolin-4,4-dimethyl-2-yl) obtained in above step is treated with phosphorous oxychloride in a polar solvent to give 2-(n-Butyl)-3-[2'cyanobiphenyl-4-ylmethyl]-4-oxo-1,3 diazaspiro[4.4]non-1-ene-4-one.

2-(n-Butyl)-3-[2'cyanobiphenyl-4-ylmethyl]-4-oxo-1,3 diazaspiro[4.4]non-1-ene-4-one of formula (VII) obtained in above step is reacted with tributyl tin azide in o-xylene at reflux temperature for 80 hours to give crude Irbesartan. The mass is treated with 1N NaOH. The phases were separated and aq. phase is washed with o-xylene and isopropyl ether. Aq phase is treated with charcoal, filtered through hyflobed and then treated with 3N HCl. The product title compound is filtered, washed with water and dried under vacuum at 60° C. The product is crystallized from 95% ethanol to give Irbesartan. (Yield: 81%)

¹H-NMR (DMSO d6): δppm 0.78 (t, 3H); 1.17-1.30 (sex, 2H); 1.40-1.50 (quent, 2H); 1.64-1.66 (m, 2H); 1.80-1.82 (m, 6H); 2.22-2.29 (t, 2H); 4.67 (s, 2H); 7.07 (s, 4H); 7.50-7.68 (m, 4H)

M⁺: 429.6

Example 7

Preparation of Irbesartan

4'aminomethyl-2-amide-1,1' biphenyl (54.3 g) (VIa, where R is CONH₂) is added to toluene (2 Liter) and methane sulfonic acid (19 ml) and stir it at ambient temperature.

1-Valeramidocyclopentanecarboxylic acid (56.3 g) (V) is added to the above solution and the mass is refluxed under stirring for 24 hours and water is separated by dean stark apparatus. Methane sulphonic acid (4 ml) is added to the reaction mixture and refluxed under stirring for 24 hours and water is separated by dean stark apparatus. The reaction mixture is cooled to ambient temperature and toluene is distilled under vacuum completely. Ethyl acetate (2 Liter) and 2N sodium hydroxide solution (320 ml) is added to the residue and stirred for 30 minutes. Two phases are separated and the organic phase is washed with brine (400 ml). The organic phase is treated with activated charcoal, filtered through hyflobed and filtrate is distilled out under vacuum completely. Methyl t-butyl ether (123 ml) is added to the residue and stirred for 2 hours at ambient temperature. The product is filtered and washed with methyl t-butyl ether (90 ml) and suck dried. The product is dried under vacuum at 50° C. till constant weight. (Yield: 80%) to give 2-(n-Butyl)-3-[2'amidebiphenyl-4-ylmethyl]-4-oxo-1,3 diazaspiro[4.4]non-1-ene-4-one.

2-(n-Butyl)-3-[2'amidebiphenyl-4-ylmethyl]-4-oxo-1,3 diazaspiro[4.4]non-1-ene-4-one of formula (VIIa, where R is —CONH$_2$) obtained in above step is treated with thionyl chloride at reflux for 3.5 hours. The reaction was filtered and the thionyl chloride removed in vacuo. The residue was dissolved in toluene and reconcentrated in vacuo. On standing overnight, the residue crystallized. The crystals were collected and washed with hexane to give 2-(n-Butyl)-3-[2'cyanobiphenyl-4-ylmethyl]-4-oxo-1,3 diazaspiro[4.4]non-1-ene-4-one.

2-(n-Butyl)-3-[2'cyanobiphenyl-4-ylmethyl]-4-oxo-1,3 diazaspiro[4.4]non-1-ene-4-one of formula (VII) obtained in above step is reacted with tributyl tin azide in o-xylene at reflux temperature for 80 hours to give crude Irbesartan. The mass is treated with 1N NaOH. The phases were separated and aq. phase is washed with o-xylene and isopropyl ether. Aq phase is treated with charcoal, filtered through hyflobed and then treated with 3N HCl. The product title compound is filtered, washed with water and dried under vacuum at 60° C. The product is crystallized from 95% ethanol to give Irbesartan. (Yield: 85%)

$^1$H-NMR (DMSO d6): δppm 0.78 (t, 3H); 1.17-1.30 (sex, 2H); 1.40-1.50 (quent, 2H); 1.64-1.66 (m, 2H); 1.80-1.82 (m, 6H); 2.22-2.29 (t, 2H); 4.67 (s, 2H); 7.07 (s, 4H); 7.50-7.68 (m, 4H)

M$^+$: 429.6

Example 8

Preparation of Irbesartan

4'aminomethyl-2-(1-triphenylmethyl-1H-tetrazol-5-yl)-1,1' biphenyl (118.46 g) (VIb, where A is triphenylmethyl protected tetrazolyl group) is added to toluene (2 Liter) and methane sulfonic acid (19 ml) and stir it at ambient temperature.

1-Valeramidocyclopentanecarboxylic acid (56.3 g) (V) is added to the above solution and the mass is refluxed under stirring for 24 hours and water is separated by dean stark apparatus. Methane sulphonic acid (4 ml) is added to the reaction mixture and refluxed under stirring for 24 hours and water is separated by dean stark apparatus. The reaction mixture is cooled to ambient temperature and toluene is distilled under vacuum completely. Ethyl acetate (2 Liter) and saturated sodium bicarbonate solution (320 ml) is added to the residue and stirred for 30 minutes. Two phases are separated and the organic phase is washed with brine (400 ml). The organic phase is treated with activated charcoal, filtered through hyflobed and filtrate is distilled out under vacuum completely. Methyl t-butyl ether (123 ml) is added to the residue and stirred for 2 hours at ambient temperature. The product is filtered and washed with methyl t-butyl ether (90 ml) and suck dried. The product is dried under vacuum at 50° C. till constant weight. (Yield: 80%) to give 2-(n-Butyl)-3-[2' (1-triphenylmethyl-1H-tetrazol-5-yl)biphenyl-4-ylmethyl]-4-oxo-1,3 diazaspiro[4.4]non-1-ene-4-one.

2-(n-Butyl)-3-[2'(1-triphenylmethyl-1H-tetrazol-5-yl)biphenyl-4-ylmethyl]-4-oxo-1,3 diazaspiro[4.4]non-1-ene-4-one of formula (VIb, where A is triphenylmethyl protected tetrazolyl group) obtained in above step was treated with 5 N HCl in methanol and tetrahydrofuran at 0-5° C. and then stirred at ambient temperature for overnight. After completion of reaction tetrahydrofuran and methanol was distilled out under vacuum. The residue was partitioned between toluene and 1N sodium hydroxide. Two phases were separated and aqueous phase was washed with isopropyl ether. The aqueous phase was adjusted to pH 4.6 by 3N hydrochloric acid. The product was filtered and washed with water and dried in air to get Irbesartan. (Yield: 75%)

$^1$H-NMR (DMSO d6): δppm 0.78 (t, 3H); 1.17-1.30 (sex, 2H); 1.40-1.50 (quent, 2H); 1.64-1.66 (m, 2H); 1.80-1.82 (m, 6H); 2.22-2.29 (t, 2H); 4.67 (s, 2H); 7.07 (s, 4H); 7.50-7.68 (m, 4H)

M$^+$: 429.6

Example 9

Preparation of 1-Valeramidocyclopentanecarboxylic acid

In a 3 necked 250 ml round bottom flask equipped with mechanical stirrer, was charged with sodium hydroxide solution (24.1 g dissolved in 100 ml water) and 1-aminocyclopentane carboxylic acid hydrochloride (25 g) and chilled to 0° C. under stirring. Tetra butyl ammonium bromide (0.25 g) was added to the reaction mixture followed by slow addition of a solution of valeroyl chloride (27.5 g) in toluene (20 ml) during one hour at 0-5° C. under stirring. The reaction mass was stirred for 1 hour at 0-5° C. The reaction mixture was diluted with water (100 ml) toluene (20 ml) and stirred for 15 minutes. The two phases were separated. The aqueous phase was washed with toluene (20 ml). Aqueous phase was chilled to 10° C. and acidified with hydrochloric acid and stirred it for 1 hour. The product was filtered and washed with water. The product was dried at 60° C. till constant weight. (Yield: 22 g; 68%).

$^1$H-NMR (DMSOd$^6$): δ ppm 0.819 (t, 3H); 1.16-128 (sex, 2H); 1.37-1.47 (quent, 2H); 1.59 (m, 4H); 1.79-1.84 (m, 2H); 1.97-2.05 (m, 4H); 8.02 (s, 1H); 12.0 (Broad singlet, 1H).

What is claimed is:

1. A process for the preparation of Irbesartan of formula (I) comprising the steps of:

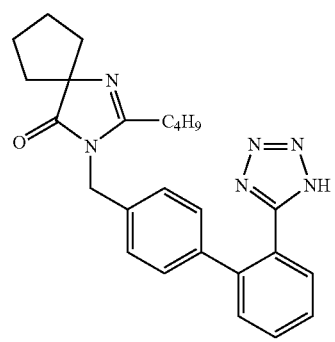

(I)

(i) reacting 4' aminomethyl-2-cyano biphenyl of formula (VI) with 1-veleramido cyclopentane carboxylic acid of formula (V)

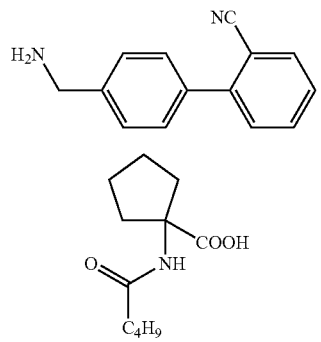

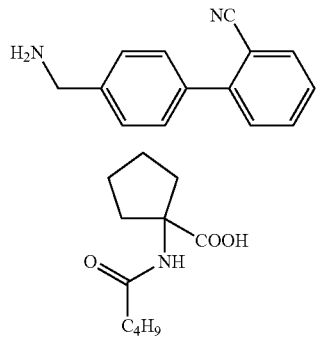

in an organic solvent and in the presence of an acid, without activating the —COOH group of compound of formula (V) to give 1-(2'cyanobiphenyl-4-yl-methylaminocarbonyl)-1-pentanoylamino cyclopentane of formula (VII)

in the presence of an acid in an organic solvent to give 1-(2'cyanobiphenyl-4-yl-methylaminocarbonyl)-1-pentanoylamino cyclopentane of formula (VII)

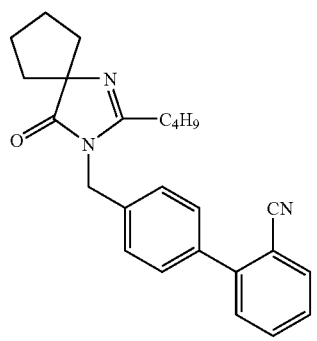

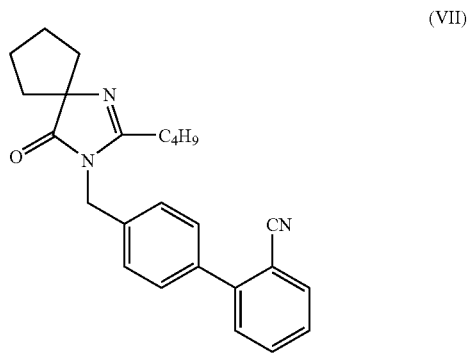

(ii) converting the compound of formula (VII) obtained in step (i) to Irbesartan of formula (I) by reacting the compound of the formula (VII) with tributyl tin azide in o-xylene to give Irbesartan of formula (I).

2. A process for the preparation of Irbesartan of formula (I) comprising step of, 3. A process for the preparation of Irbesartan of formula (I) comprising the steps of:

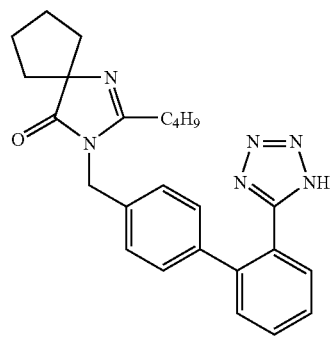

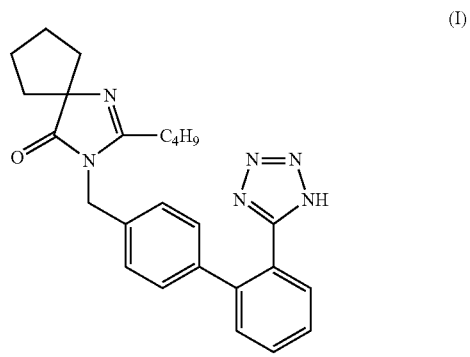

reacting 4' aminomethyl-2-cyano biphenyl of formula (VI) with 1-veleramido cyclopentane carboxylic acid of formula (V)

(i) reacting 4' aminomethyl-2-cyano biphenyl of formula (VI) with 1-veleramido cyclopentane carboxylic acid of formula (V)

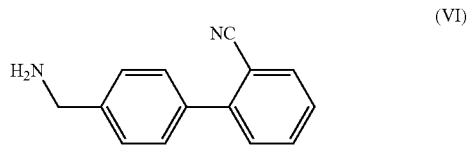

-continued

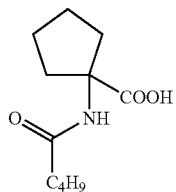
(V)

in an organic solvent and in the presence of an acid to give 1-(2'cyanobiphenyl-4-yl-methylaminocarbonyl)-1-pentanoylamino cyclopentane of formula (VII)

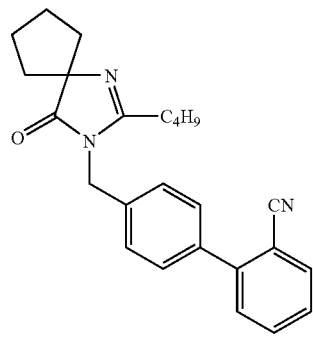
(VII)

(ii) converting the compound of formula (VII) obtained in step (i) to Irbesartan of formula (I) by reacting the compound of the formula (VII) with tributyl tin azide in o-xylene to give Irbesartan of formula (I).

4. The process as claimed in claim 1, wherein said acid is selected from the group consisting of organic and inorganic acids or mixture thereof.

5. The process as claimed in claim 2, wherein said acid is selected from the group consisting of organic and inorganic acids or mixture thereof.

6. The process as claimed in claim 3, wherein said acid is selected from the group consisting of organic and inorganic acids or mixture thereof.

7. The process as claimed in claim 4, wherein the organic acid is selected from the group comprising methane sulfonic acid and p-toluene sulfonic acid.

8. The process as claimed in claim 5, wherein the organic acid is selected from the group comprising methane sulfonic acid and p-toluene sulfonic acid.

9. The process as claimed in claim 6, wherein the organic acid is selected from the group comprising methane sulfonic acid and p-toluene sulfonic acid.

10. The process as claimed in claim 4, wherein the inorganic acid is sulfuric acid.

11. The process as claimed in claim 5, wherein the inorganic acid is sulfuric acid.

12. The process as claimed in claim 6, wherein the inorganic acid is sulfuric acid.

13. The process as claimed in claim 1, wherein said organic solvent is selected from the group consisting of $C_{1-8}$ aromatic hydrocarbons or mixture thereof.

14. The process as claimed in claim 2, wherein said organic solvent is selected from the group consisting of $C_{1-8}$ aromatic hydrocarbons or mixture thereof.

15. The process as claimed in claim 3, wherein said organic solvent is selected from the group consisting of $C_{1-8}$ aromatic hydrocarbons or mixture thereof.

16. The process as claimed in claim 13 wherein $C_{1-8}$ aromatic hydrocarbons is toluene.

17. The process as claimed in claim 14 wherein $C_{1-8}$ aromatic hydrocarbons is toluene.

18. The process as claimed in claim 15 wherein $C_{1-8}$ aromatic hydrocarbons is toluene.

19. A process for the preparation of Irbesartan of formula (I) comprising step of,

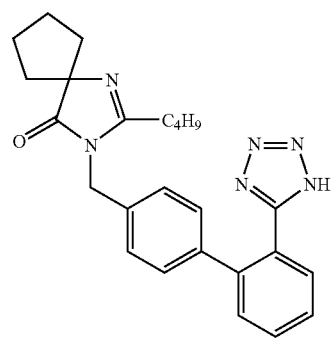
(I)

reacting biphenyl derivative of formula (VIa)

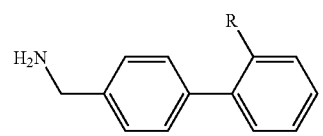
(VIa)

wherein R represents a group selected from —$CONH_2$ or compound of formula

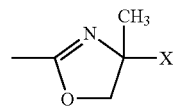

wherein X represents H or $C_{1-4}$ alkyl, preferably methyl;
or any other such group which can be converted to cyano group,
with 1-veleramido cyclopentane carboxylic acid of formula (V)

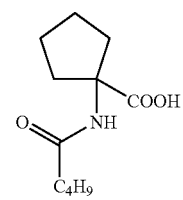
(V)

in the presence of an acid in an organic solvent to give biphenyl derivative of formula (VIIa)

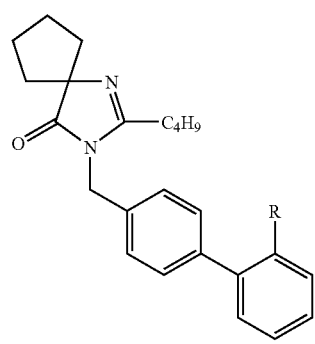

(VIIa)

wherein R has the same meaning as mentioned hereinabove.

20. A process for the preparation of Irbesartan of formula (I) comprising steps of:

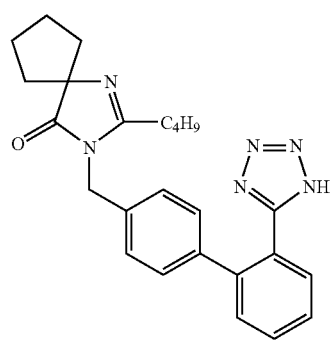

(I)

(i) reacting biphenyl derivative of formula (VIa)

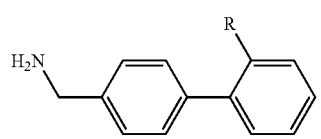

(VIa)

wherein R represents a group selected from —CONH$_2$ or compound of formula

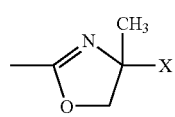

wherein X represents H or C$_{1-4}$ alkyl, preferably methyl; or any other such group which can be converted to cyano group, with 1-veleramido cyclopentane carboxylic acid of formula (V),

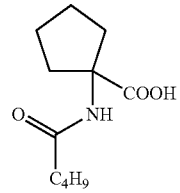

(V)

in the presence of an acid in an organic solvent to give biphenyl derivative of formula (VIIa);

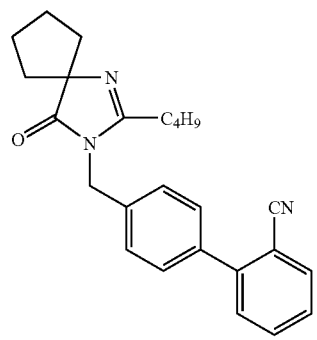

(VIIa)

wherein R has the same meaning as mentioned hereinabove (ii) converting the compound of formula (VIIa) to compound of formula (VII);

(VII)

(iii) converting the compound of formula (VII) obtained in step (ii) to Irbesartan of formula (I) by reacting the compound of the formula (VII) with tributyl tin azide in o-xylene to give Irbesartan of formula (I).

21. The process as claimed in claim 19, wherein said acid is selected from the group consisting of organic and inorganic acids or mixture thereof.

22. The process as claimed in claim 20, wherein said acid is selected from the group consisting of organic and inorganic acids or mixture thereof.

23. The process as claimed in claim 21, wherein the organic acid is selected from the group comprising methane sulfonic acid and p-toluene sulfonic acid.

24. The process as claimed in claim 22, wherein the organic acid is selected from the group comprising methane sulfonic acid and p-toluene sulfonic acid.

25. The process as claimed in claim 21, wherein the inorganic acid is sulfuric acid.

26. The process as claimed in claim 22, wherein the inorganic acid is sulfuric acid.

27. The process as claimed in claim 19, wherein said organic solvent is selected from the group consisting of $C_{1-8}$ aromatic hydrocarbons or mixture thereof.

28. The process as claimed in claim 20, wherein said organic solvent is selected from the group consisting of $C_{1-8}$ aromatic hydrocarbons or mixture thereof.

29. The process as claimed in claim 27 wherein $C_{1-8}$ aromatic hydrocarbons is toluene.

30. The process as claimed in claim 28 wherein $C_{1-8}$ aromatic hydrocarbons is toluene.

31. A process for the preparation of Irbesartan of formula (I) comprising step of,

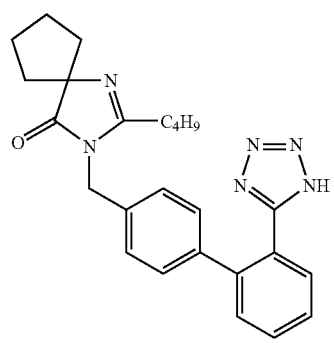
(I)

reacting biphenyl derivative of formula (VIb)

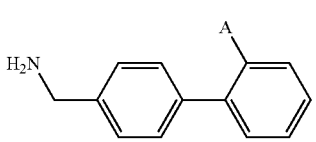
(VIb)

wherein A represents protected tetrazoyl group
with 1-veleramido cyclopentane carboxylic acid of formula (V)

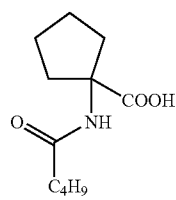
(V)

in the presence of an acid in an organic solvent to give biphenyl derivative of formula (VIIb)

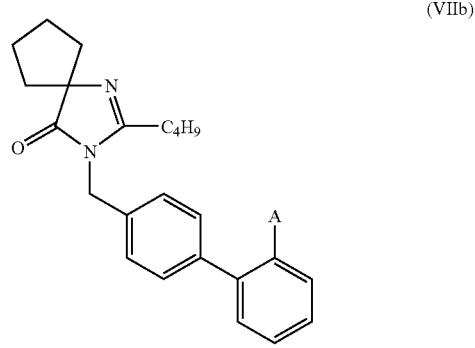
(VIIb)

wherein A has the same meaning as mentioned hereinabove.

32. A process for the preparation of Irbesartan of formula (I) comprising steps of:

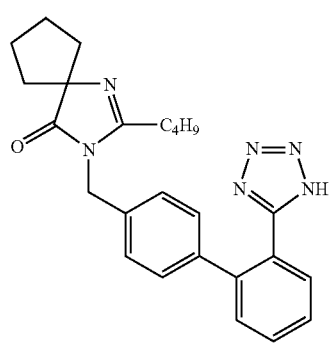
(I)

(i) reacting biphenyl derivative of formula (VIb)

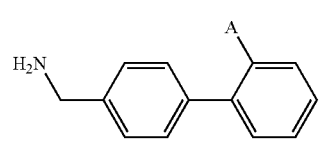
(VIb)

wherein A represents protected tetrazoly group
with 1-veleramido cyclopentane carboxylic acid of formula (V)

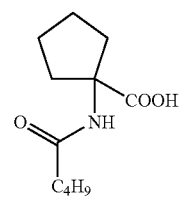
(V)

in the presence of an acid in an organic solvent to give biphenyl derivative of formula (VIIb)

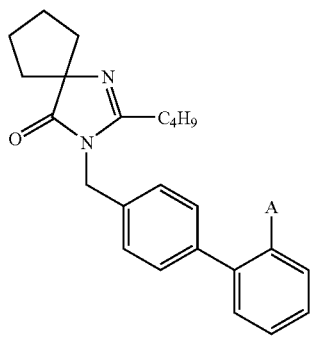

(VIIb)

wherein A has the same meaning as mentioned hereinabove (ii) deprotecting the protected tetrazolyl group present in the compound of formula (VIIb) to Irbesartan of formula (I) by hydrolysis or hydrogenolysis.

33. The process as claimed in claim 31, wherein said acid is selected from the group consisting of organic and inorganic acids or mixture thereof.

34. The process as claimed in claim 32, wherein said acid is selected from the group consisting of organic and inorganic acids or mixture thereof.

35. The process as claimed in claim 33, wherein the organic acid is selected from the group comprising methane sulfonic acid and p-toluene sulfonic acid.

36. The process as claimed in claim 34, wherein the organic acid is selected from the group comprising methane sulfonic acid and p-toluene sulfonic acid.

37. The process as claimed in claim 33, wherein the inorganic acid is sulfuric acid.

38. The process as claimed in claim 34, wherein the inorganic acid is sulfuric acid.

39. The process as claimed in claim 31, wherein said organic solvent is selected from the group consisting of $C_{1-8}$ aromatic hydrocarbons or mixture thereof.

40. The process as claimed in claim 32, wherein said organic solvent is selected from the group consisting of $C_{1-8}$ aromatic hydrocarbons or mixture thereof.

41. The process as claimed in claim 39 wherein $C_{1-8}$ aromatic hydrocarbons is toluene.

42. The process as claimed in claim 40 wherein $C_{1-8}$ aromatic hydrocarbons is toluene.

43. A process for the preparation of 1-veleramidocyclopentane carboxylic acid of formula (V) comprising,

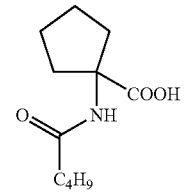

(V)

reacting Aminocyclopentane carboxylic acid hydrochloride salt of formula (IV)

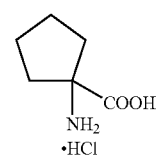

(IV)

with valeroyl chloride in the presence of a base and a phase transfer catalyst (PTC) in a suitable solvent and water to give 1-veleramido cyclopentane carboxylic acid of formula (V).

44. A process of preparation of Irbesartan comprising the steps of:

(i) reacting Aminocyclopentane carboxylic acid hydrochloride salt of formula (IV)

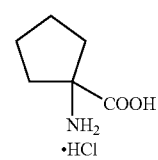

(IV)

with valeroyl chloride in the presence of a base and a phase transfer catalyst (PTC) in a suitable solvent and water to give 1-veleramido cyclopentane carboxylic acid of formula (V)

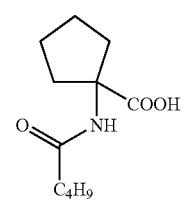

(V)

(ii) reacting 4' aminomethyl-2-cyano biphenyl of formula (VI) with 1-veleramido cyclopentane carboxylic acid of formula (V)

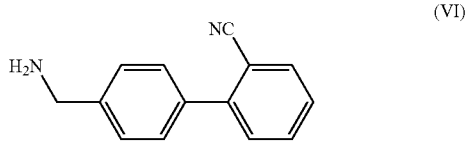

(VI)

in the presence of an acid in an organic solvent to give 1-(2'cyanobiphenyl-4-yl-methylaminocarbonyl)-1-pentanoylamino cyclopentane of formula (VII).

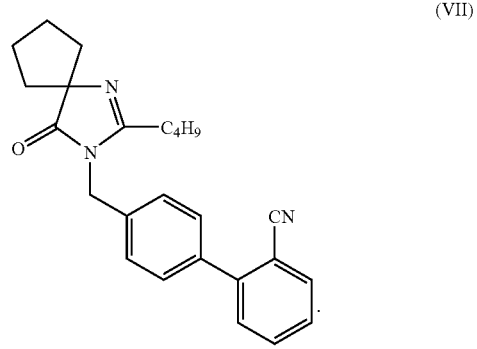

(VII)

45. The process as claimed in claim 43, wherein the phase transfer catalyst is selected from the group comprising quarternery ammonium compound, phosphonium compound and cyclic polyethers.

46. The process as claimed in claim 44, wherein the phase transfer catalyst is selected from the group comprising quarternery ammonium compound, phosphonium compound and cyclic polyethers.

47. The process as claimed in claim 45, wherein the phase transfer catalyst is selected from the group tetrabutyl ammonium bromide (TBAB), tetrabutyl ammonium hydrogensulfate, benzalkonium chloride, cetyl trimethyl ammonium chloride or mixture thereof.

48. The process as claimed in claim 46, wherein the phase transfer catalyst is selected from the group tetrabutyl ammonium bromide (TBAB), tetrabutyl ammonium hydrogensulfate, benzalkonium chloride, cetyl trimethyl ammonium chloride or mixture thereof.

49. The process as claimed in claim 43, wherein the suitable solvent is selected from the group comprising non polar water immiscible solvent.

50. The process as claimed in claim 44, wherein the suitable solvent is selected from the group comprising non polar water immiscible solvent.

51. The process as claimed in claim 49, wherein the suitable solvent is selected from toluene, xylene, benzene, dichloromethane, cyclohexane, hexane, heptane and the mixture thereof.

52. The process as claimed in claim 50, wherein the suitable solvent is selected from toluene, xylene, benzene, dichloromethane, cyclohexane, hexane, heptane and the mixture thereof.

53. The process as claimed in claim 43, wherein the base is selected from alkali metal hydroxide, alkaline earth metal carbonate or bicarbonate.

54. The process as claimed in claim 44, wherein the base is selected from alkali metal hydroxide, alkaline earth metal carbonate or bicarbonate.

55. The process as claimed in claim 53, wherein the base is selected from NaOH or KOH, LiOH, $Na_2CO_3$, $K_2CO_3$, $KHCO_3$, $NaHCO_3$, $CaCO_3$ or mixture thereof.

56. The process as claimed in claim 54, wherein the base is selected from NaOH or KOH, LiOH, $Na_2CO_3$, $K_2CO_3$, $KHCO_3$, $NaHCO_3$, $CaCO_3$ or mixture thereof.

57. The process as claimed in claim 44, wherein said acid is selected from the group consisting of organic and inorganic acids or mixture thereof.

58. The process as claimed in claim 57, wherein the organic acid is selected from the group comprising methane sulfonic acid and p-toluene sulfonic acid.

59. The process as claimed in claim 57, wherein the inorganic acid is sulfuric acid.

60. The process as claimed in claim 44, wherein said organic solvent is selected from the group consisting of $C_{1-8}$ aromatic hydrocarbons or mixture thereof.

61. The process as claimed in claim 60 wherein $C_{1-8}$ aromatic hydrocarbons is toluene.

62. A process for the preparation of Irbesartan of formula (I) comprising the steps of:

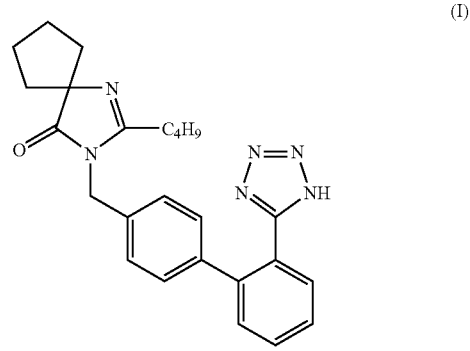

(I)

(i) reacting 4' aminomethyl-2-cyano biphenyl of formula (VI) with 1-veleramido cyclopentane carboxylic acid of formula (V)

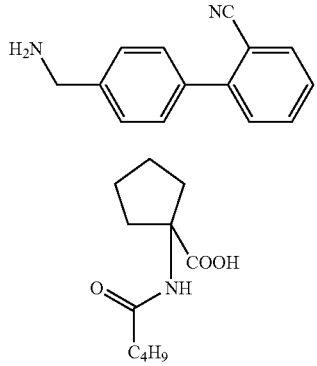

(VI)

(V)

in toluene and in the presence of methane sulfonic acid, without activating the —COOH group of compound of formula (V) and without isolating open chain compound of formula (VIII) to give 1-(2'cyanobiphenyl-4-yl-methylaminocarbonyl)-1-pentanoylamino cyclopentane of formula (VII)

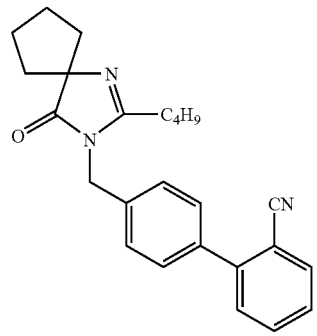

(VII)

(ii) converting the compound of formula (VII) obtained in step (i) to Irbesartan of formula (I) by reacting the compound of the formula (VII) with tributyl tin azide in o-xylene to give Irbesartan of formula (I).

63. A pharmaceutical composition comprising Irbesartan as prepared according to claim 62 as active ingredient.

* * * * *